United States Patent
Tebbe

[19]

[11] Patent Number: 5,922,336
[45] Date of Patent: Jul. 13, 1999

[54] MICROCAPSULE-COATED MATERIAL

[75] Inventor: Gerold Tebbe, Monaco, Monaco

[73] Assignee: Deotexix Inc., Germany

[21] Appl. No.: 08/773,822

[22] Filed: Dec. 27, 1996

Related U.S. Application Data

[30] Foreign Application Priority Data

Jan. 3, 1996 [DE] Germany ............................ 196 00 076

[51] Int. Cl.[6] ............................ A41D 19/00; A41D 13/10
[52] U.S. Cl. ............................ 424/402; 424/400; 2/159; 2/164; 2/168; 2/169
[58] Field of Search .................................. 424/402, 400; 2/154, 164, 168, 169

[56] References Cited

U.S. PATENT DOCUMENTS

| | | |
|---|---|---|
| 3,896,807 | 7/1975 | Buchalter . |
| 4,567,065 | 1/1986 | Schneiderman . |
| 4,996,052 | 2/1991 | McIntosh . |
| 5,138,719 | 8/1992 | Orlianges et al. . |
| 5,549,924 | 8/1996 | Shienker et al. . |

FOREIGN PATENT DOCUMENTS

| | | |
|---|---|---|
| 0 328 937 | 8/1989 | European Pat. Off. . |
| 2604869 | 4/1988 | France . |
| 35 45 926 | 7/1987 | Germany . |

OTHER PUBLICATIONS

Gonzales, Gloves Fingerless Mittens and Mitts Bearing a Covering of Microcapules Containing a Cosmetic or Pharmaceutical Product (Abstract), Source: GPI and WPAT, Apr. 15, 1988.

*Primary Examiner*—Thurman K. Page
*Assistant Examiner*—Brian K. Seidleck

[57] ABSTRACT

For the purpose of applying, over the surface of the skin, active substances which irritate the skin or smell bad. A glove is manufactured from foil with a coating that contains microcapsules that can be burst open by pressure, and the active substance applied to the skin.

18 Claims, 6 Drawing Sheets

MICROCAPSULE-COATED MATERIAL

BACKGROUND OF THE INVENTION

FIELD OF THE INVENTION

This application claims the priority of German patent application 196 00 076.9, filed Jan. 3, 1996.

The invention relates to a microcapsule-coated, flexible carrier material, and more particularly, to a microcapsule-coated flexible material constructed as a glove.

Flexible carrier materials, particularly in the form of cloths that have a coating with microcapsules that can contain different materials, are known per se. When the microcapsule-coated side of such a carrier material is rubbed with pressure on a surface, the microcapsules burst open and the material contained therein is released and applied to the surface.

Experience has shown that in cloths with a microcapsule coating large parts of the cloth remain unused, since only certain portions of the cloth are effected when the cloth is rubbed under pressure. A large part of the expensive microencapsulated material remains unused. Furthermore, one must be careful to maintain the contact between hand and cloth, particularly if the surface to which the microencapsulated material is to be applied is substanially inclined. In addition, using a microcapsule-coated cloth can lead to applying encapsulated material at a point where it is not desired. Pressure may be inadvertently exerted on parts of the cloth that cover a point where encapsulated material is not desired. This may occur, for example, when one attempts to prevent the cloth from falling.

SUMMARY OF THE INVENTION

The object of the invention is to provide a flexible carrier material with a microencapsulating coating in a form that is easier to manipulate and allows better utilization of the microencapsulated material. This object is achieved by a microcapsule-coated flexible carrier material in which the carrier material is constructed as a glove having a form of a rectangular pocket.

For many applications, it is advantageous if the flexible carrier material with the microcapsule coating can be drawn, in a tight-fitting manner, over the hand or part of the hand in the fashion of a glove. This permits optimum utilization of the microcapsule coating and also is as easy as possible to manipulate, because pressure can be readily exerted with the hand on all points on the glove over which the microcapsule coating is attached, and firm contact between the carrier material and the hand is automatically guaranteed. Furthermore, it is possible, with the aid of such a carrier material in the form of a glove, to avoid the inadvertent application of the microencapsulated material at points where it is not desired. The tight fit of the glove makes it possible to precisely control the position of the point at which pressure is exerted. The inadvertent exertion of pressure, for example as a result of an attempt to catch the falling carrier material, is avoided.

The invention allows manufacture of the glove without waste, since it is based on rectangular pockets.

In one embodiment, the glove can be pulled over the index, middle, ring, and little fingers and ends above the base of the thumb.

Advantageously, the glove has a tightening means that allows for lateral play of the hand in the rectangular pocket. This allows the manufacture of the glove in a single size. The glove can be drawn together, as needed, according to the size of the user's hand and thereby guarantees a tight fit on the hand.

Additionally, the glove has a means for adhering the glove to the skin. This ensures a tight fit.

Advantageously, the means to tighten the glove and achieve adhesion to the skin are achieved through the use of an angled strap.

Optimum utilization of the microcapsule coating is achieved when the microencapsulated coating covers no more than the upper two-thirds of one or both faces of the glove.

When the microencapsulated coating is applied to the palm of the glove. Economical use of the microencapsulated material is achieved, particularly when it is applied to a convex surface.

Advantageously, the microencapsulated coating may be applied to the outer side of the hand of the glove. This proves advantageous because the coating is applied to an essentially flat surface.

In one embodiment, the glove is open at the finger end. This is advantageous when, during the application of the microencapsulated material, the fingertips are intended to perform an additional function, for example, to apply a polishing agent. Such a rectangularly-shaped glove is open on both ends, which allows it to be pulled on from both ends.

The surface that constitutes the outer side of the glove may be napped or fluffy. In this way, the surface of the glove carrying the microcapsules is particularly large. The napped or fluffy character is also advantageous for successfully wiping the released liquid content of the capsule off of the skin after the microcapsules have burst open.

The carrier material may be a composite material made of a thin, inner base layer that is impermeable to the content of the microcapsules and a napped or fluffy working area. This makes it possible to use a very heavily napped or fluffy outer layer that does not provide a reliable blocking function. The thin, inner layer provides the blocking function.

The microcapsules may contain an active substance that irritates the skin, for example, an active substance for locally increasing circulation, such as bee poison or the like. Alternatively, the microcapsule may contain a bad-smelling substance, such as a fly repel ant. These are preferred applications in the field of medicaments.

The microcapsules may be a mixture of microcapsules of differing durability with respect to their wall material or thickness. This allows the substances in the capsules to be released in succession or in a predetermined sequence, for example, with the application of only light pressure and then with the application of higher pressure. In this way, it is possible first to lubricate the surface of the skin and then rub an active substance onto the skin that acts on the surface of the skin, but need not penetrate into the interior of the skin (or is not intended to penetrate into the interior of the skin).

BRIEF DESCRIPTION OF THE DRAWINGS

Preferred embodiments of the invention will now be described, taken together with the drawings, in which.

DETAILED DESCRIPTION OF PREFERRED EMBODIMENTS

Figure 1:
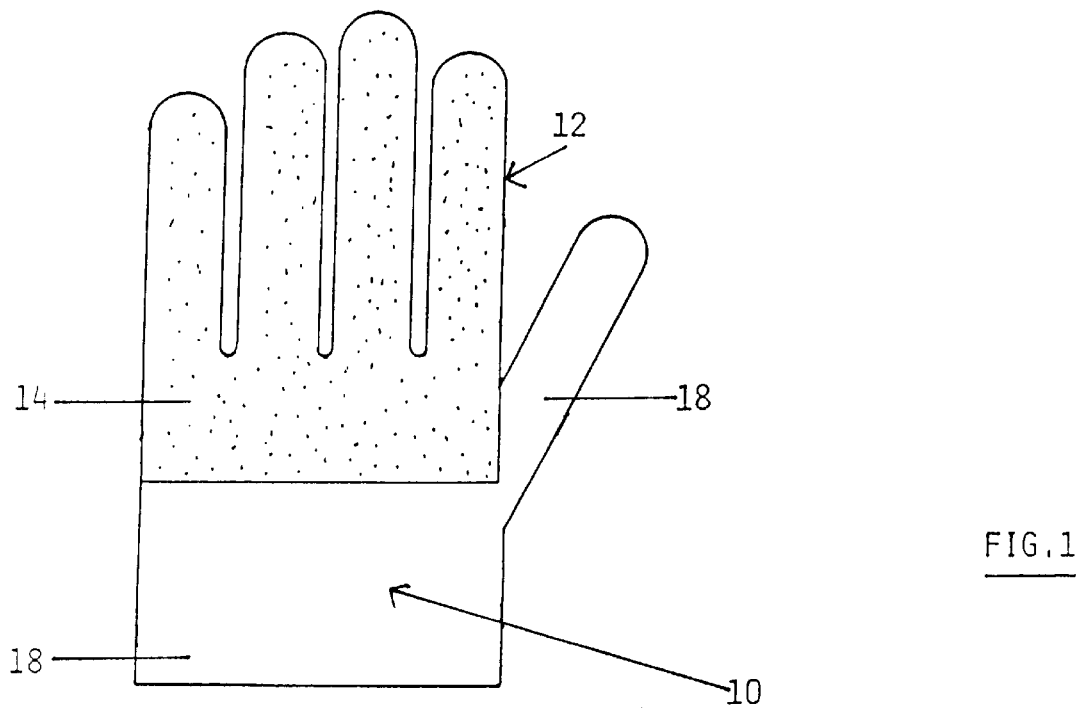
FIG. 1 shows the palm of a microcapsule-coated, flexible glove.
Figure 2:
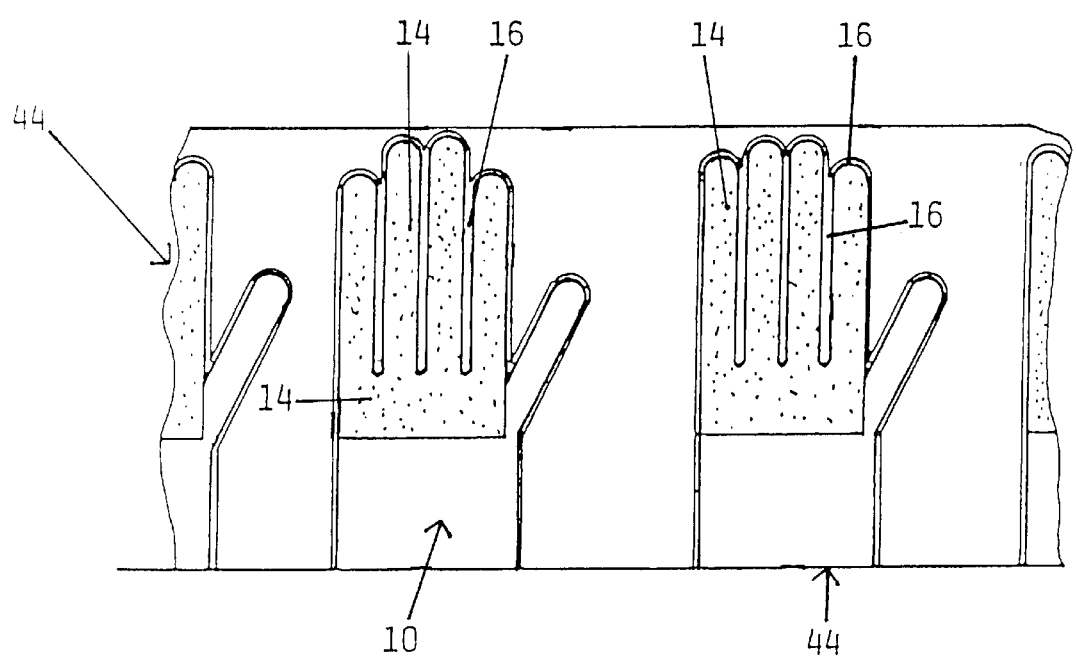
FIG. 2 shows one side of a double-ply strip of endless material, from which individual gloves can be separated off, with the seams and microcapsule coating already attached.

FIGS. 1 and 2 show the palm 10 of a glove 12 which, in part, carries a coating 14 made of microcapsules. At the same time, separating welds forming seams 16 connect two superimposed plies of a flexible carrier material 18.

Any materials which can be coated with microcapsules 14 which burst open under pressure are possible as the flexible carrier material 18. Examples of these are weldable foils which accept bonding agents, for example polyethylene foils that are provided with a napped surface, for example by coronal discharge. Particular preference is given to materials which contain non-woven fabric for example non-woven cellulose fabric, with thermoplastic fibres, since on the one hand, double layers of such non-woven fabric can be easily welded to form gloves 12, and on the other hand, non-woven fabrics have an open structure and therefore receive microcapsules easily and in fairly large quantities. Besides welding, the seams 16 of the glove 12 can also be produced in some other way, for example by stitching or adhesion.

FIG. 2 shows a double-ply strip 44 of endless material for gloves 12 according to FIG. 1.

In the case of separating welds, the separation of the gloves 12, which are initially in the form of an endless strip 44, can take place by pulling them apart or else, for example, by means of scissors, a matrix, a hot knife or a laser beam.

The microcapsule coating 14 is applied before or after the manufacture of the seams 16, and expediently before the separation of the gloves 12. It can be applied over the entire glove or only over parts of the glove. Preferably, the microcapsulated coating is applied over the upper two thirds of the glove or parts thereof, for example over the uppermost or middle third of the glove or its upper half.

Microcapsules can generally be fastened to a carrier material by sticking or pressing them on. In the case of pressing them on, the pressure must be limited in order to avoid bursting open the microcapsules. Thus gelatin capsules, for example, can be stuck on by means of gelatin dissolved in a slightly volatile solvent, or they may be rolled on by means of a surface that has been made sticky or stickier.

Microencapsulated materials in which a carrier material is in the form of a glove are particularly useful for protective or impregnating layers. For example, shoe cleaning cream (where precise and metered application is made possible). Or, these applications can be used to avoid over metering, such as in lubricating applications for technical components (in order to avoid an expensive excess); for body care applications such as deodorant or perfume (for precisely metered application) and percutaneous drugs (likewise for precisely metered application).

Figure 3:
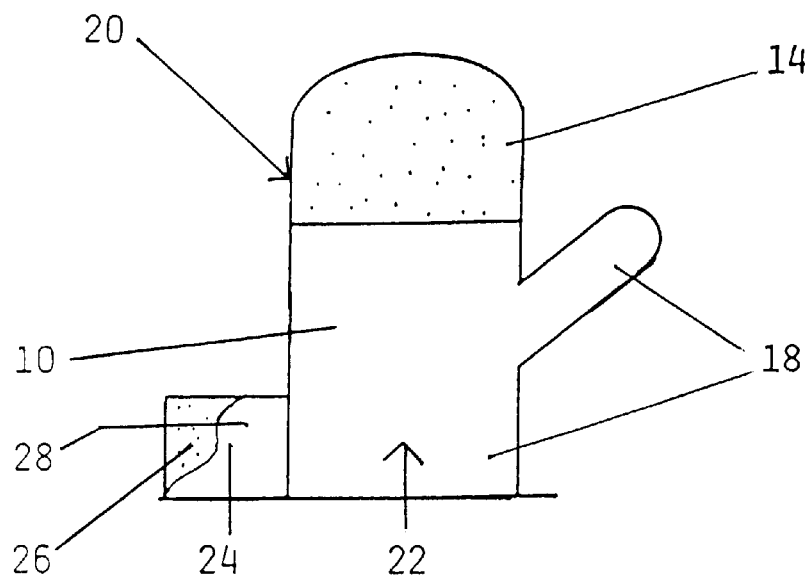
FIG. 3 shows the palm of a mitten, the upper third of which is coated with microcapsules and that has a means for tightening at the wrist.

FIG. 3 shows the palm 10 of a flexible carrier material 18 constructed as a mitten 20. The upper third of the mitten carries a microcapsule coating 14 and has a tightening strap 22 at the wrist. As a rule, the tightening strap 22 is attached to the lower edge of the glove 20 in such a way that it terminates at the edge of the glove, but it does not have to do so. In any case, it has a part 24 which projects laterally beyond the right or left-hand edge of the glove 20.

The tightening strap 22 can be attached before or after the separation of the gloves 20. All types of attachment are possible, for example, stitching-on, welding-on or sticking-on; particular preference being given to sticking-on. The protruding part 24 of the tightening strap carries an adhesive layer 26 for fixing to the glove 20 after tightening. The adhesive is provided in such a way that the adhesive closure can be opened again after use. Before use, the adhesive layer 26 is protected by a covering 28 that can be pulled off.

Other methods of fixing the tightening strap to the glove, for example a velcro-type closure, are possible, depending on the nature of the carrier material.

Figure 4:
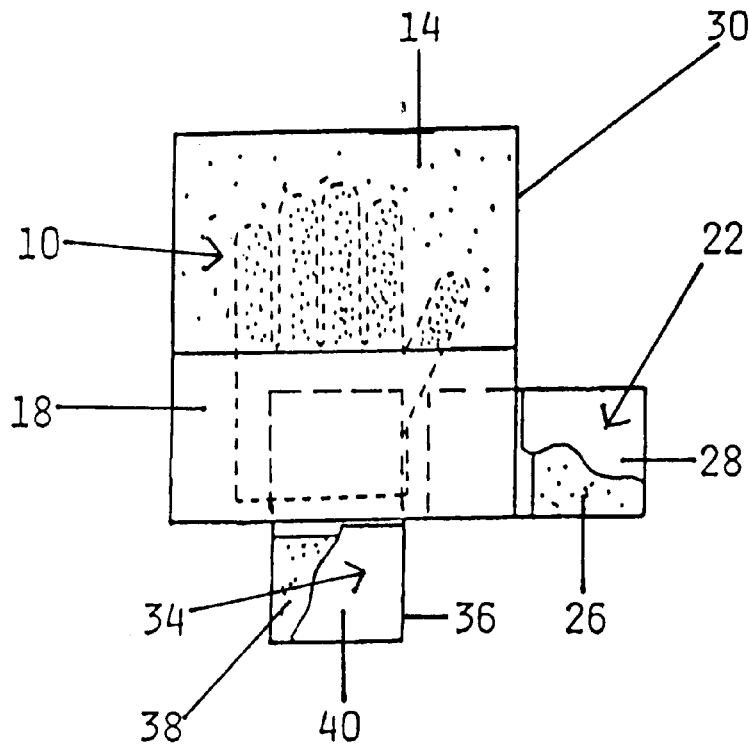
FIG. 4 shows the palm of a glove that is made of flexible carrier material and that has the shape of a rectangular pocket.

FIG. 4 shows a rectangular glove 30. The upper half of the palm 10 has a coating 14 with microcapsules. Disposed on the outer side of the rectangular glove 30 is a tightening strap 22 and a sticking flap 34 for sticking to the skin. On a part 36 that protrudes beyond the edge contour of the glove, the sticking strap 34 has a layer of adhesive 38, such as is known in a similar manner from adhesive bandages, which is kind to the skin. This layer is protected, before use, by a covering 40 that can be pulled off. The tightening strap 22 is constructed as described in the case of FIG. 3.

Figure 5:
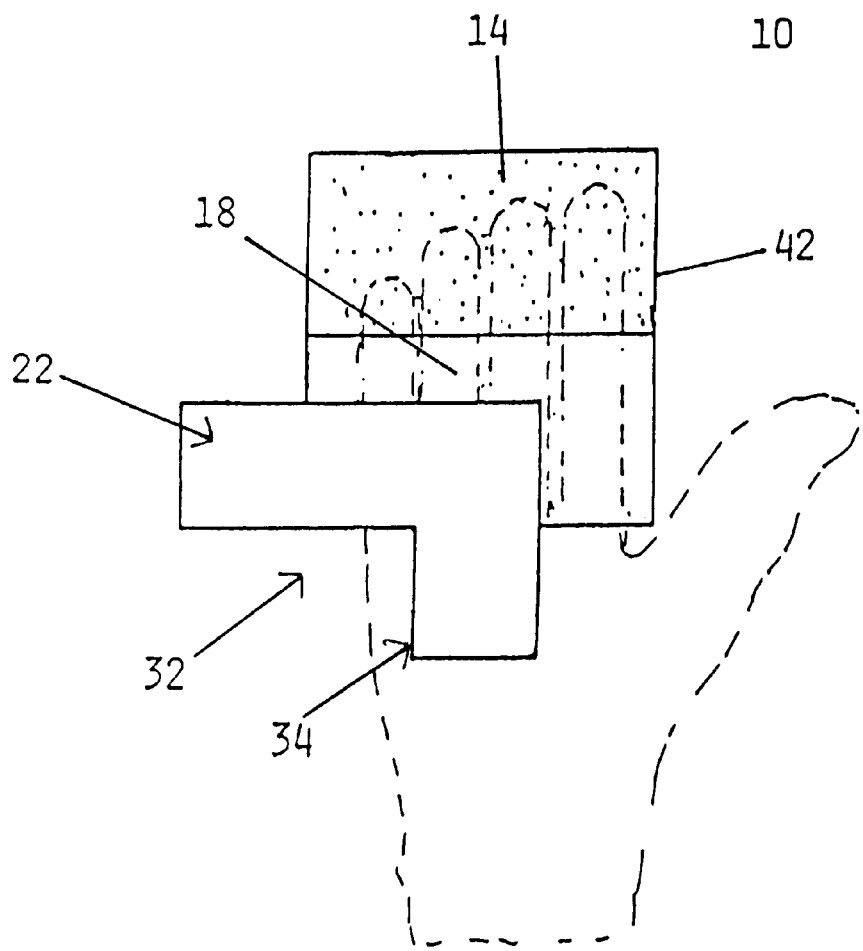
FIG. 5 shows the palm of a glove that is in the form of a rectangular pocket and that is drawn only over the index, middle, ring and little fingers.

FIG. 5 shows a rectangular glove 42, the length of which is so dimensioned that it can be pulled over the index, middle, ring and little fingers and ends above the base of the thumb. The upper half of the palm 10 of the rectangular glove 42 carries a microcapsule coating 14. There is also provided, on the palm 10 of the glove 42 an angled combination strap 32, of which those parts that protrude beyond the edges of the glove serve for tightening the glove and for sticking it to the skin, respectively.

Figure 6:
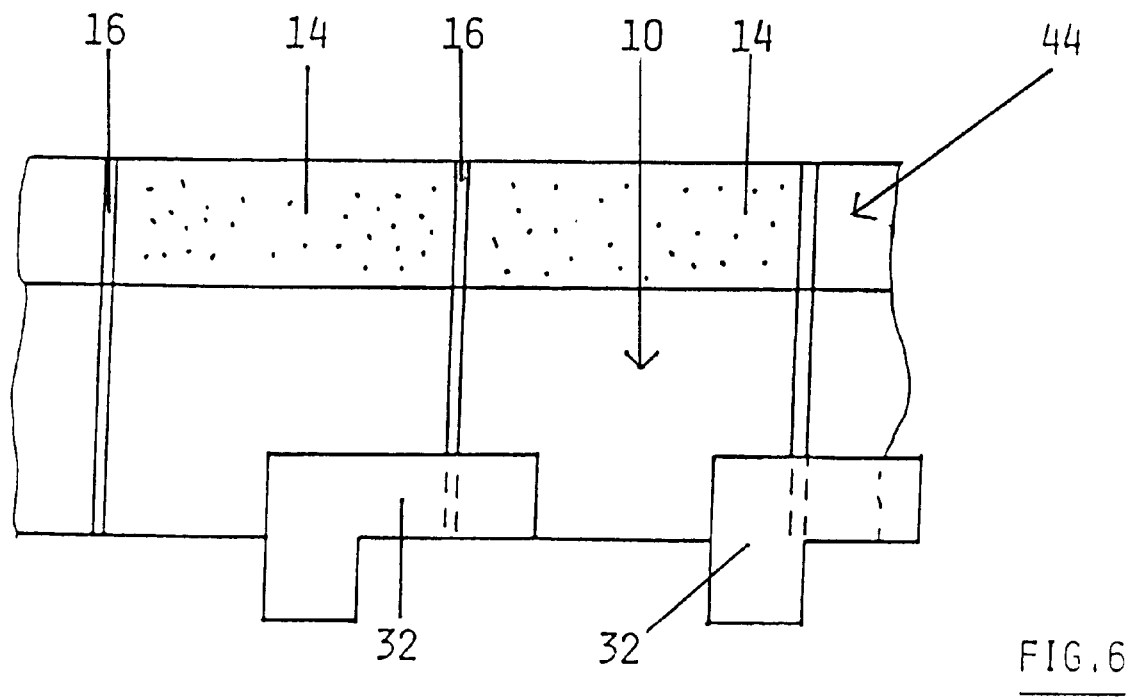
FIG. 6 shows the upper side of a double-ply strip of endless material, from which the rectangular gloves illustrated in FIG. 5 can be separated off.

FIG. 6 shows one side of a strip 44 of endless material. The side forms the palms 10 of rectangular gloves 30, 42, after the latter have been separated. The seams 16 and the microcapsule coating 14 are already attached. The combination straps 32 are attached before separation of the gloves from the strip 44 of endless material. However, it is also possible for the straps to be attached only the separation of the gloves 30, 42. The rectangular shape of the glove makes it possible to use the strip 44 of endless material without waste, and permits the easiest application of the microcapsule coating 14, since no, empty spaces have to be taken into account. This is very economical.

In a modification to the embodiments according to FIGS. 1 to 5, the gloves may also be constructed in such a way that they are open at the finger end. In the preferred embodiments according to FIGS. 4 and 5, therefore, they assume the shape of a sleeve.

In the preferred embodiments according to FIGS. 1 to 5, either the palm 10 alone, or both the palm 10 and the outer side (not shown) of the hand of the glove, can be coated with microcapsules. In the latter case, the microcapsule coating 14 may likewise extend over only part of the side. The coated parts on the two sides may be of different size. Thus, for example, the upper two thirds or the upper half of the palm 10 may be coated, whereas on the outer side of the hand, the carrier material 18 is coated only over the upper half or the upper third of the glove.

In a further modification to the embodiments in FIGS. 1 to 5, the reference numerals 10 in these figures may relate to the outer side of the hand of the corresponding gloves, in which case the palms (now not shown) are not coated with microcapsules.

In a further modification of the invention, it is possible to coat one face of the glove with a first microencapsulated material (for example skin oil) and the other face of the glove with a second microencapsulated material (for example fly-repelling oil). In this event, the two sides of the glove are preferably differentiated by color, for example a carrier material which has different printing or is permeated by a different color, different colored wall material for the microcapsules or different coloring for the contents of microcapsule which are at least partially translucent.

Figure 7:
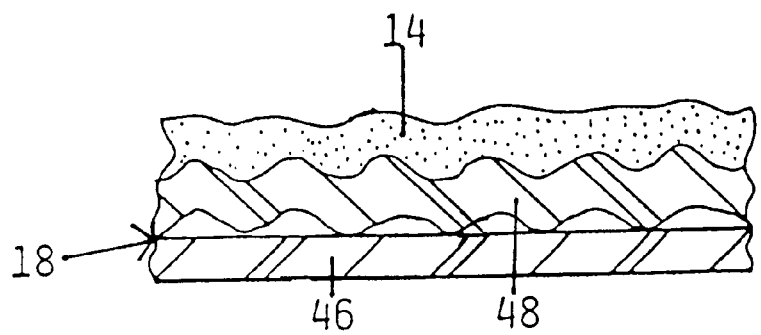
FIG. 7 shows an enlarged section through one region of a first carrier material for use in a microcapsule coated glove.

In the carrier material represented in FIG. 7, a working layer 48 is applied to a base layer 46. The base layer 46 consists of a flexible, thin plastic foil that is impermeable to the contents of the microcapsules. The working layer 48 is a plastic foil that is corrugated by mechanical and/or thermal treatment, so that it is given a larger surface and has a fluffy feel, similar to that of a fiber nap. The working layer 48 is attached to the base layer 46 by thermal treatment or by using a thin layer of adhesive. Located above the working layer 48 is the coating 14, which is applied by scraping it on.

Figure 8:
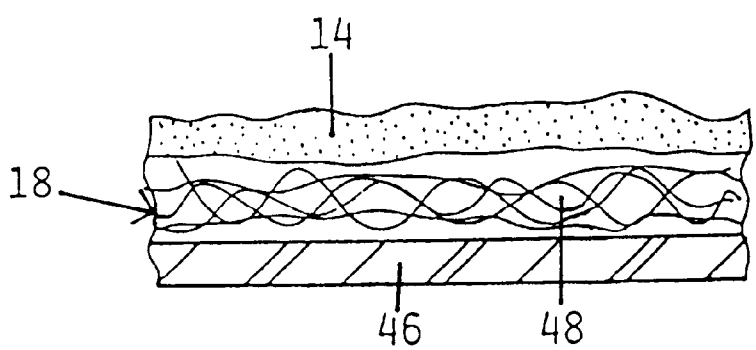
FIGS. 8 and 9 show sections that are similar to that in FIG. 7, but in which modified carrier materials are shown.

The preferred embodiment according to FIG. 8 largely corresponds to that according to FIG. 7, except that a non-woven fabric is used as the working layer 48.

Figure 9:
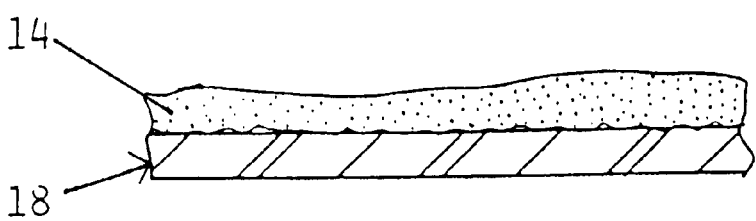

In the preferred embodiment according to FIG. 9, the carrier material 18 is a single layer which, even from the outset, has an outer surface with a good feel. The carrier material may be a plastic foil that is roughened on the outer side by coronal discharge. Alternatively, use may also be made of a dense, weldable non-woven fabric consisting of, for example, 70% polypropylene and 30% viscose material.

The weight per unit area of the carrier materials described above preferably lies, in total, below 100 g/m, and preferably in the range between 60 and 80 g/m. Such materials have good flexibility and can also be successfully applied between toes and fingers.

Figure 10:
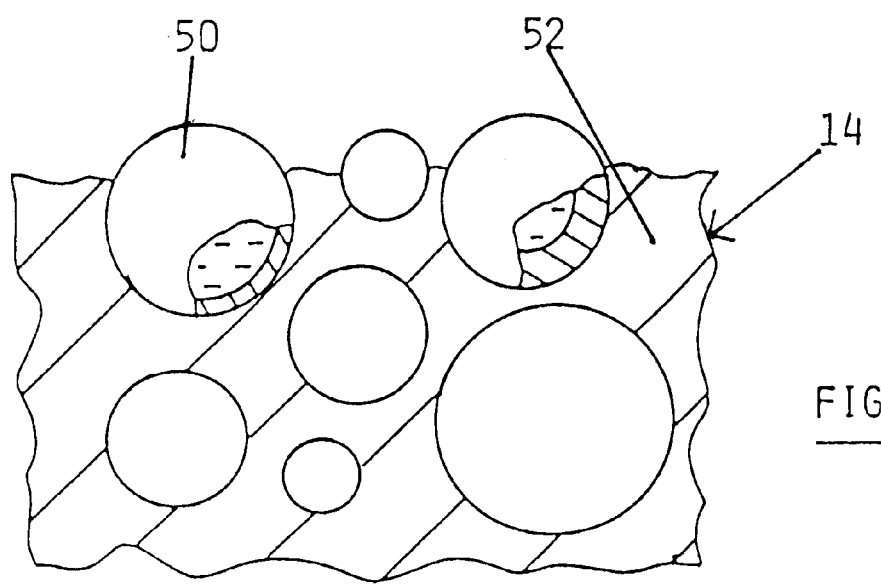
FIG. 10 shows a further enlarged section, through a partial region of a coating layer of the carrier materials in FIGS. 7 to 9.
Figure 11:
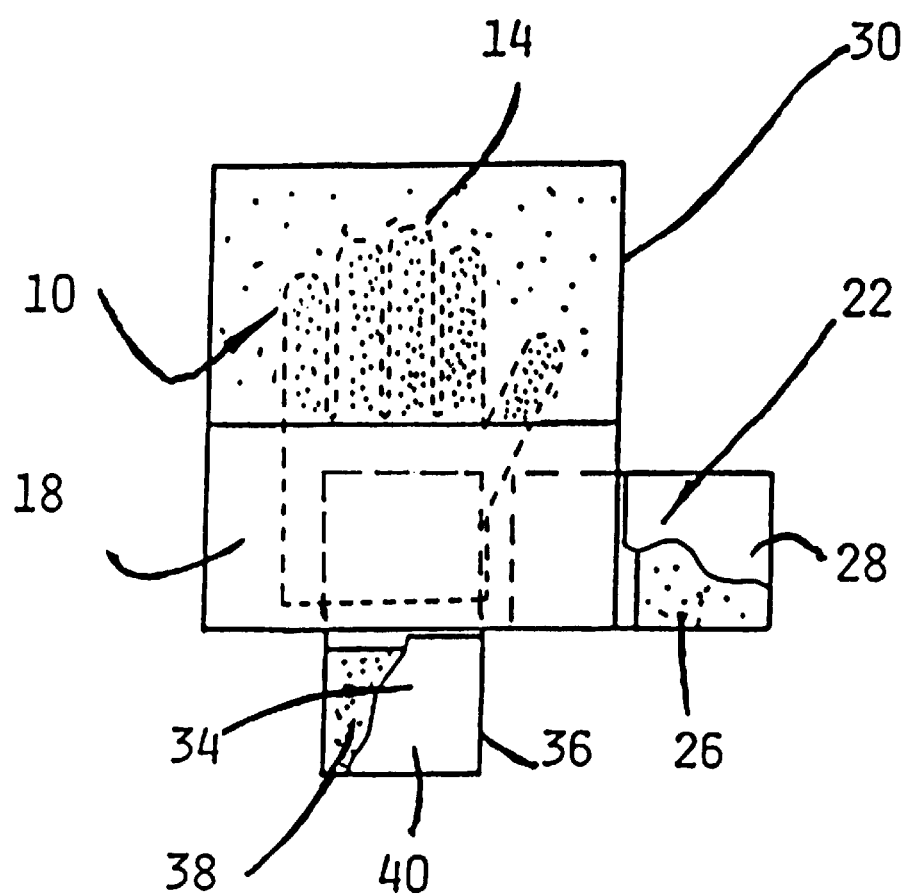
FIG. 11 shows a glove having the form of a rectangular pocket wherein the glove accommodates the whole hand.

As can be seen from FIG. 10, the coating 14 contains microcapsules 50 of different diameter. The microcapsules 50 are held together in the layer by a weak, brittle bonding agent 52. Under the microcapsules 50 are additional microcapsules with a high wall thickness and a low wall thickness, so that some of the microcapsules break even under light pressure, while some break under medium pressure, and some break only when high pressure is applied.

If desired, it is also possible to incorporate different liquids in the microcapsules of different mechanical strength, for example an oil for closing the pores of the skin in microcapsules that are easily breakable, and a fly-repelling agent that is intended to take effect on the surface of the skin, in microcapsules that are less easily breakable.

I claim:

1. A microcapsule-coated (14), flexible carrier material (18), wherein the carrier material (18) is constructed as a glove (12; 20; 30; 42) having a form of a rectangular pocket, wherein the glove accommodates a whole hand and has microcapsules coated thereon that have at least one of active and inactive ingredients therein.

2. A carrier material as claimed in claim 1, wherein the glove has a tightening means (22) that allows for lateral play of the hand in the rectangular pocket.

3. A carrier material as claimed in claim 1, wherein the glove additionally has a means (34) for achieving adhesion to the skin.

4. A carrier material as claimed in claim 2, wherein the tightening means (22) and means (34) for achieving adhesion to the skin are jointly constituted by an angled strap (32).

5. A carrier material as claimed in claim 1, wherein the applied microcapsule coating (14) covers no more than the upper two thirds of one or both of the faces of the glove.

6. A carrier material as claimed in claim 1, wherein the microcapsule coating (14) is applied to the palm (10) of the glove.

7. A carrier material as claimed in claim 1, wherein the microcapsule coating (14) is applied to the outer side of the hand of the glove.

8. A carrier material as claimed in claim 1, wherein the glove is open at the finger end.

9. A carrier material as claimed in claim 1, wherein the surface which constitutes the outer side of the glove is napped or fluffy.

10. A carrier material as claimed in claim 9, wherein the surface is a composite material made of a thin, inner base layer (46) which is impermeable to the contents of the microcapsules, and of a napped or fluffy working layer (48).

11. A carrier material as claimed in claim 1, wherein the microcapsules contain an active substance that irritates the skin for locally increasing the circulation, such as bee poison.

12. A carrier material as claimed in claim 1, wherein-the microcapsules (50) are a mixture of microcapsules of different durability which differ in respect of their wall material and/or in respect of their wall thickness.

13. A carrier material as claimed in claim 1, wherein the microcapsules contain an active substance for locally increasing circulation.

14. A carrier material as claimed in claim 1, wherein the microcapsules contain bee poison.

15. A carrier material as claimed in claim 1, wherein the microcapsules (50) contain a fly-repelling substance.

16. A microcapsule-coated (14), flexible carrier material (18), wherein the carrier material (18) is constructed as a glove (12; 20; 30; 42) having a form of a rectangular pocket, wherein the glove (42) can be pulled over the index, middle, ring and little fingers and ends above the base of the thumb and has microcapsules coated thereon that have at least one of active and inactive ingredients therein.

17. A microcapsule-coated (14), flexible carrier material (18) according to claim 1, wherein the microcapsules are selected from the group consisting of protective impregnating substances, shoe cleaning substances, insect repellants, lubricating agents, bad smelling substances, skin oils, perfumes, deodorants, percutaneous drugs, skin drugs, skin caring agents, skin irritating substances, substances for locally increasing blood circulation, and polishing agents.

18. A microcapsule-coated (14), flexible carrier material (18) according to claim 16, wherein the microcapsules are selected from the group consisting of protective impregnating substances, shoe cleaning substances, insect repellents, lubricating agents, bad smelling substances, skin oils, perfumes, deodorants, percutaneous drugs, skin drugs, skin caring agents, skin irritating substances, substances for locally increasing blood circulation, and polishing agents.

* * * * *